(12) United States Patent
Shimazaki

(10) Patent No.: US 7,448,997 B2
(45) Date of Patent: Nov. 11, 2008

(54) ULTRASONIC PULSE TRANSMISSION METHOD AND ULTRASONIC DIAGNOSTIC APPARATUS

(75) Inventor: Tadashi Shimazaki, Tokyo (JP)

(73) Assignee: GE Medical Systems Global Technology Company, LLC., Waukesha, WI (US)

( * ) Notice: Subject to any disclaimer, the term of this patent is extended or adjusted under 35 U.S.C. 154(b) by 0 days.

(21) Appl. No.: 10/698,310

(22) Filed: Oct. 31, 2003

(65) Prior Publication Data

US 2004/0102702 A1 May 27, 2004

(30) Foreign Application Priority Data

Nov. 7, 2002 (JP) ............................ 2002-323988

(51) Int. Cl.
*A61B 8/00* (2006.01)

(52) U.S. Cl. .................. 600/437; 600/443; 600/459

(58) Field of Classification Search ................ 600/437, 600/447, 459, 443
See application file for complete search history.

(56) References Cited

U.S. PATENT DOCUMENTS

| 5,152,294 | A | * | 10/1992 | Mochizuki et al. .......... 600/459 |
| 5,212,667 | A | | 5/1993 | Tomlinson, Jr. et al. |
| 5,301,670 | A | | 4/1994 | Sato et al. |
| 5,460,179 | A | * | 10/1995 | Okunuki et al. ............. 600/444 |
| 5,657,054 | A | * | 8/1997 | Files et al. ................... 345/177 |
| 5,908,391 | A | * | 6/1999 | Muzilla et al. .............. 600/454 |
| 5,980,458 | A | * | 11/1999 | Clark .......................... 600/437 |
| 6,039,692 | A | * | 3/2000 | Kristoffersen .............. 600/454 |
| 6,086,537 | A | * | 7/2000 | Urbano et al. .............. 600/443 |
| 6,099,471 | A | | 8/2000 | Torp et al. |
| 6,126,601 | A | | 10/2000 | Gilling |
| 6,159,153 | A | * | 12/2000 | Dubberstein et al. ........ 600/443 |
| 6,425,868 | B1 | * | 7/2002 | Tamura ....................... 600/454 |
| 6,488,629 | B1 | * | 12/2002 | Sætre et al. ................. 600/443 |
| 6,537,217 | B1 | * | 3/2003 | Bjærum et al. ............. 600/441 |
| 6,701,341 | B1 | * | 3/2004 | Wu et al. ..................... 709/200 |

FOREIGN PATENT DOCUMENTS

| JP | 09-066055 | 3/1997 |
| JP | 2001-178720 | 7/2001 |

OTHER PUBLICATIONS

A Japanese language Notice Reasons for Rejection from the Japanese Patent Office.

* cited by examiner

*Primary Examiner*—Brian L. Casler
*Assistant Examiner*—John F Ramirez
(74) *Attorney, Agent, or Firm*—Armstrong Teasdale LLP

(57) ABSTRACT

For the purpose of preventing noticeable interleave blocks on a display screen, when a number of packets P is defined, P ($\geq 2$) ultrasonic pulse transmissions are conducted in one direction to acquire one acoustic line signal. At that time, if a number of interleaves I is defined, the ultrasonic pulse transmissions in the one direction are each interleaved with ultrasonic pulse transmissions for acquiring (I−1) acoustic line signals that belong to (I−1) frames different from the frame to which the former acoustic line signal belongs.

6 Claims, 6 Drawing Sheets

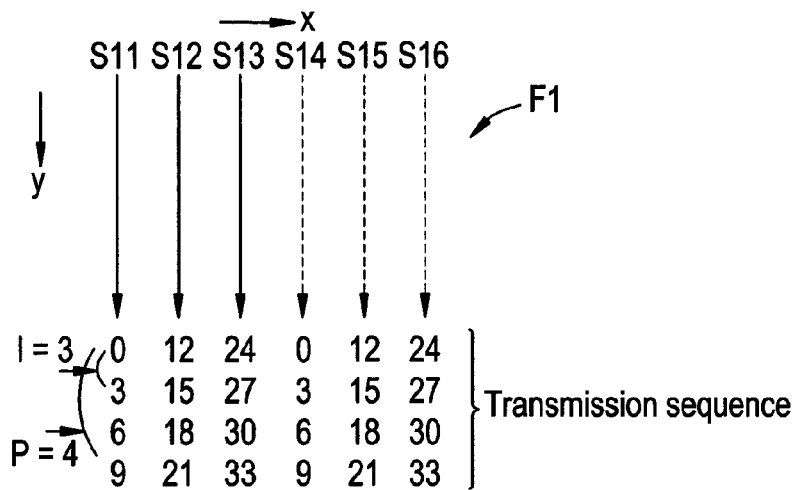
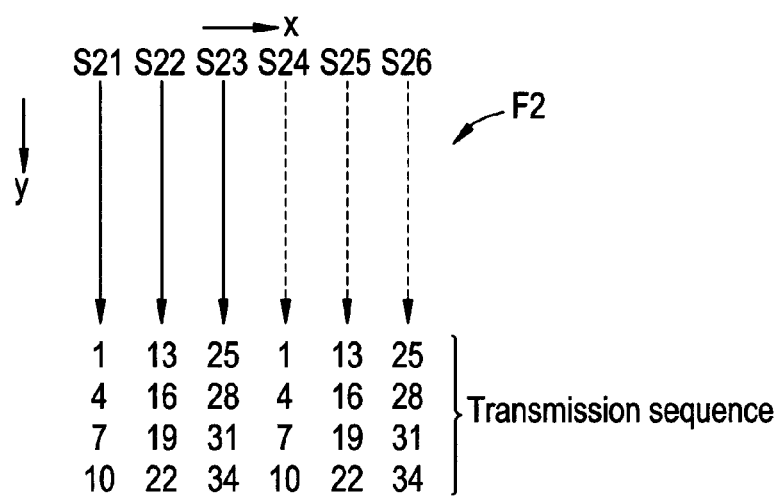
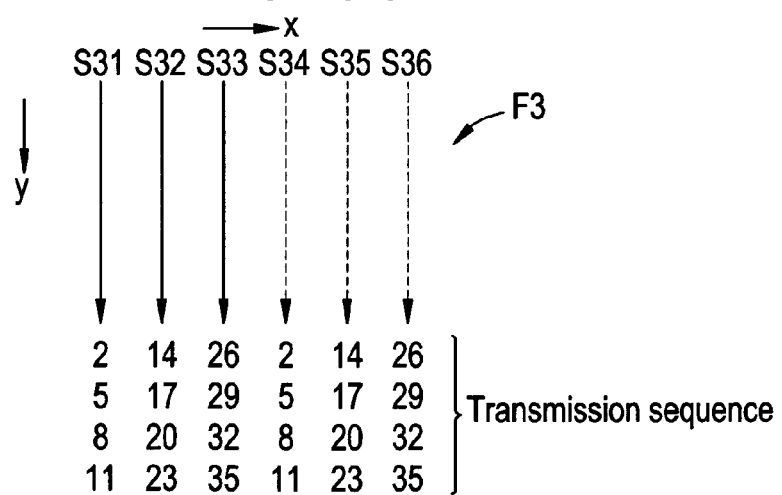

ULTRASONIC PULSE TRANSMISSION METHOD AND ULTRASONIC DIAGNOSTIC APPARATUS

CROSS REFERENCE TO RELATED APPLICATIONS

This application claims the benefit of Japanese Application No. 2002-323988 filed Nov. 7, 2002.

BACKGROUND OF THE INVENTION

The present invention relates to an ultrasonic pulse transmission method and an ultrasonic diagnostic apparatus, and more particularly to an ultrasonic pulse transmission method and an ultrasonic diagnostic apparatus that can prevent noticeable interleave blocks on a display screen.

Japanese Patent Application Laid Open No. H3-126442 discloses an interleaving scanning technique involving, when a number of packets P ($\geq 2$) is defined for conducting P ultrasonic pulse transmissions in one direction to acquire one acoustic line signal, interleaving an ultrasonic pulse transmission for acquiring a different acoustic line signal between the ultrasonic pulse transmissions in the one direction.

When the number of ultrasonic pulse transmissions in the different directions interleaved between the ultrasonic pulse transmissions in the one direction is defined as (I−1), I is referred to as the number of interleaves. I is defined as I$\geq$2.

As an example, if the number of packets P=2, the number of interleaves I=3, and one frame is composed of acoustic lines lined up in a sequence of acoustic line 1, acoustic line 2, acoustic line 3, acoustic line 4, . . . , then ultrasonic pulse transmissions are done in the following order:

acoustic line 1-acoustic line 2-acoustic line 3-acoustic line 1-acoustic line 2-acoustic line 3-acoustic line 4-acoustic line 5-acoustic line 6-acoustic line 4-acoustic line 5-acoustic line 6-acoustic line 7-acoustic line 8-acoustic line 9-acoustic line 7-acoustic line 8-acoustic line 9- . . .

In this example, interleaving is achieved by unitary acoustic line groups each comprised of the number of interleaves of adjacent acoustic lines, such as acoustic lines 1-3, acoustic lines 4-6, acoustic lines 7-9, and so forth. These acoustic line groups, each of which serves as a unit of interleaving, are called interleave blocks.

Since the conventional interleaving scanning conducts interleaving within one frame, the one frame is constituted by concatenating a plurality of interleave blocks.

However, the difference in scan time between acoustic lines at a boundary of adjacent interleave blocks is larger than the difference in scan time between acoustic lines within an interleave block, which leads to a problem that difference in image quality occurs across interleave blocks, resulting in noticeable interleave blocks on an image.

SUMMARY OF THE INVENTION

It is therefore an object to provide an ultrasonic pulse transmission method and an ultrasonic diagnostic apparatus that can prevent noticeable interleave blocks on a display screen.

In its first aspect, the present invention provides an ultrasonic pulse transmission method characterized in comprising: when a number of packets P ($\geq 2$) is defined for conducting P ultrasonic pulse transmissions in one direction to acquire one acoustic line signal, interleaving at least one ultrasonic pulse transmission for acquiring an acoustic line signal that belongs to a frame different from that to which said former acoustic line signal belongs between the ultrasonic pulse transmissions in said one direction.

The ultrasonic pulse transmission method of the first aspect conducts interleaving not within one frame but across a plurality of frames. Thus, a frame becomes free of interleave blocks, thereby preventing noticeable interleave blocks on a display screen.

To implement the ultrasonic pulse transmission method, an ultrasonic diagnostic apparatus that can electronically or mechanically change the ultrasonic pulse transmission direction in two directions, one being a direction in which acoustic lines are lined up within one frame, the other being a direction in which two or more frames are laid.

In its second aspect, the present invention provides the ultrasonic pulse transmission method having the aforementioned configuration, characterized in comprising: when a number of interleaves I ($\geq 2$) is defined, interleaving ultrasonic pulse transmissions for acquiring (I−1) acoustic line signals that belong to (I−1) frames different from the frame to which said former acoustic line signal belongs between the ultrasonic pulse transmissions in said one direction.

The ultrasonic pulse transmission method of the second aspect conducts interleaving not within one frame but across I frames. Thus, a frame becomes free of interleave blocks, thereby preventing noticeable interleave blocks on a display screen.

In its third aspect, the present invention provides an ultrasonic pulse transmission method characterized in comprising: when a number of packets P ($\geq 2$) is defined for conducting P ultrasonic pulse transmissions in one direction to acquire one acoustic line signal, allowing selection between interleaving at least one ultrasonic pulse transmission for acquiring another acoustic line signal that belongs to the frame to which said former acoustic line signal belongs between the ultrasonic pulse transmissions in said one direction, and interleaving at least one ultrasonic pulse transmission for acquiring an acoustic line signal that belongs to a frame different from that to which said former acoustic line signal belongs between the ultrasonic pulse transmissions in said one direction.

According to the ultrasonic pulse transmission method of the third aspect, a mode in which interleaving is achieved within one frame or a mode in which interleaving is achieved across a plurality of frames can be selected. Thus, an appropriate mode can be selected according to an application of interleaving scanning.

In its fourth aspect, the present invention provides the ultrasonic pulse transmission method having the aforementioned configuration, characterized in comprising: when a number of interleaves I ($\geq 2$) is defined, interleaving ultrasonic pulse transmissions for acquiring (I−1) other acoustic line signals that belong to the frame to which said former acoustic line signal belongs between the ultrasonic pulse transmissions in said one direction, or interleaving ultrasonic pulse transmissions for acquiring (I−1) acoustic line signals that belong to (I−1) frames different from the frame to which said former acoustic line signal belongs between the ultrasonic pulse transmissions in said one direction.

According to the ultrasonic pulse transmission method of the fourth aspect, a mode in which interleaving is achieved by a unit of I acoustic lines within one frame or a mode in which interleaving is achieved across I frames can be selected. Thus, an appropriate mode can be selected according to an application of interleaving scanning.

In its fifth aspect, the present invention provides the ultrasonic pulse transmission method having the aforementioned configuration, characterized in comprising: electronically changing the ultrasonic pulse transmission direction among acoustic line signals that belong to the same frame, and also electronically changing the ultrasonic pulse transmission direction among acoustic line signals that belong to different frames.

According to the ultrasonic pulse transmission method of the fifth aspect, an ultrasonic probe that can electronically change the ultrasonic pulse transmission direction in two directions, one being a direction in which acoustic lines line up within one frame, the other being a direction in which two or more frames are laid, can be used.

In its sixth aspect, the present invention provides the ultrasonic pulse transmission method having the aforementioned configuration, characterized in comprising: electronically changing the ultrasonic pulse transmission direction among acoustic line signals that belong to the same frame, and mechanically changing the ultrasonic pulse transmission direction among acoustic line signals that belong to different frames.

According to the ultrasonic pulse transmission method of the sixth aspect, an ultrasonic probe that can electronically change the ultrasonic pulse transmission direction in a direction in which acoustic lines line up within one frame, and mechanically change the ultrasonic pulse transmission direction in a direction in which two or more frames are laid, can be used.

In its seventh aspect, the present invention provides the ultrasonic pulse transmission method having the aforementioned configuration, characterized in comprising: conducting ultrasonic pulse transmissions simultaneously in different directions to simultaneously acquire a plurality of acoustic line signals.

According to the ultrasonic pulse transmission method of the seventh aspect, an ultrasonic probe that can transmit ultrasonic pulses simultaneously in two or more transmission directions can be used.

In its eighth aspect, the present invention provides the ultrasonic pulse transmission method having the aforementioned configuration, characterized in comprising: acquiring acoustic line signals containing flow information.

The ultrasonic pulse transmission method of the eighth aspect can prevent noticeable interleave blocks on a display screen in collecting three-dimensional data by a CF (color flow) or B-flow technique.

In its ninth aspect, the present invention provides an ultrasonic diagnostic apparatus characterized in comprising: an ultrasonic probe; number-of-frames defining means for defining a number of frames f; number-of-packets defining means for defining a number of packets P ($\geq 2$); transmitting/receiving means for driving said ultrasonic probe to conduct P ultrasonic pulse transmissions in one direction and receive echoes to acquire an acoustic line signal; and transmission direction control means for controlling the transmission direction to interleave at least one ultrasonic pulse transmission for acquiring an acoustic line signal that belongs to a frame different from that to which said former acoustic line signal belongs between the ultrasonic pulse transmissions in said one direction.

The ultrasonic diagnostic apparatus of the ninth aspect can suitably implement the ultrasonic pulse transmission method of the first aspect.

In its tenth aspect, the present invention provides the ultrasonic diagnostic apparatus having the aforementioned configuration, characterized in that: said apparatus comprises number-of-interleaves defining means for defining a number of interleaves I ($\geq 2$); and said transmission direction control means controls the transmission direction to interleave ultrasonic pulse transmissions for acquiring (I–1) acoustic line signals that belong to (I–1) frames different from the frame to which said former acoustic line signal belongs between the ultrasonic pulse transmissions in said one direction.

The ultrasonic diagnostic apparatus of the tenth aspect can suitably implement the ultrasonic pulse transmission method of the second aspect.

In its eleventh aspect, the present invention provides an ultrasonic diagnostic apparatus characterized in comprising: an ultrasonic probe; number-of-frames defining means for defining a number of frames f; number-of-packets defining means for defining a number of packets P ($\geq 2$); transmitting/receiving means for driving said ultrasonic probe to conduct P ultrasonic pulse transmissions in one direction and receive echoes to acquire an acoustic line signal; transmission direction control means for controlling the transmission direction in an intra-frame mode in which the transmission direction is controlled to interleave at least one ultrasonic pulse transmission for acquiring another acoustic line signal that belongs to the frame to which said former acoustic line signal belongs between the ultrasonic pulse transmissions in said one direction, or in an inter-frame mode in which the transmission direction is controlled to interleave at least one ultrasonic pulse transmission for acquiring an acoustic line signal that belongs to a frame different from that to which said former acoustic line signal belongs between the ultrasonic pulse transmissions in said one direction; and interleave mode selecting means for an operator to select between said intra-frame mode and inter-frame mode.

The ultrasonic diagnostic apparatus of the eleventh aspect can suitably implement the ultrasonic pulse transmission method of the third aspect.

In its twelfth aspect, the present invention provides the ultrasonic diagnostic apparatus having the aforementioned configuration, characterized in that: said apparatus comprises number-of-interleaves defining means for defining a number of interleaves I ($\geq 2$); and said transmission direction control means controls the transmission direction to interleave ultrasonic pulse transmissions for acquiring (I–1) other acoustic line signals that belong to the frame to which said former acoustic line signal belongs between the ultrasonic pulse transmissions in said one direction, or to interleave ultrasonic pulse transmissions for acquiring (I–1) acoustic line signals that belong to (I–1) frames different from the frame to which said former acoustic line signal belongs between the ultrasonic pulse transmissions in said one direction.

The ultrasonic diagnostic apparatus of the twelfth aspect can suitably implement the ultrasonic pulse transmission method of the fourth aspect.

In its thirteenth aspect, the present invention provides the ultrasonic diagnostic apparatus having the aforementioned configuration, characterized in that: said ultrasonic probe is a two-dimensional array ultrasonic probe; and said transmission direction control means electronically changes the ultrasonic pulse transmission direction among acoustic line signals that belong to the same frame, and also electronically changes the ultrasonic pulse transmission direction among acoustic line signals that belong to different frames.

The ultrasonic diagnostic apparatus of the thirteenth aspect can suitably implement the ultrasonic pulse transmission method of the fifth aspect.

In its fourteenth aspect, the present invention provides the ultrasonic diagnostic apparatus having the aforementioned configuration, characterized in that: said apparatus comprises a mechanism that can mechanically change orientation of said ultrasonic probe in a direction orthogonal to a frame; and said transmission direction control means electronically changes the ultrasonic pulse transmission direction among acoustic line signals that belong to the same frame, and mechanically changes the ultrasonic pulse transmission direction among acoustic line signals that belong to different frames.

The ultrasonic diagnostic apparatus of the fourteenth aspect can suitably implement the ultrasonic pulse transmission method of the sixth aspect.

In its fifteenth aspect, the present invention provides the ultrasonic diagnostic apparatus having the aforementioned configuration, characterized in that: said transmitting/receiving means conducts ultrasonic pulse transmissions simultaneously in different directions to simultaneously acquire a plurality of acoustic line signals.

The ultrasonic diagnostic apparatus of the fifteenth aspect can suitably implement the ultrasonic pulse transmission method of the seventh aspect.

In its sixteenth aspect, the present invention provides the ultrasonic diagnostic apparatus having the aforementioned configuration, characterized in that: said transmitting/receiving means acquires acoustic line signals containing flow information.

The ultrasonic diagnostic apparatus of the sixteenth aspect can suitably implement the ultrasonic pulse transmission method of the eighth aspect.

According to the ultrasonic pulse transmission method and ultrasonic diagnostic apparatus of the present invention, when collecting three-dimensional data by a CF or B-flow technique in real-time, for example, and producing a projection image for display, noticeable interleave blocks on a display screen can be prevented.

Further objects and advantages of the present invention will be apparent from the following description of the preferred embodiments of the invention as illustrated in the accompanying drawings.

BRIEF DESCRIPTION OF THE DRAWINGS

FIG. 5 is an explanatory diagram showing a case in which the inter-frame mode is applied when transmission is conducted simultaneously in two transmission directions.

DETAILED DESCRIPTION OF THE INVENTION

The present invention will now be described in more detail with reference to embodiments shown in the accompanying drawings.

Figure 1:
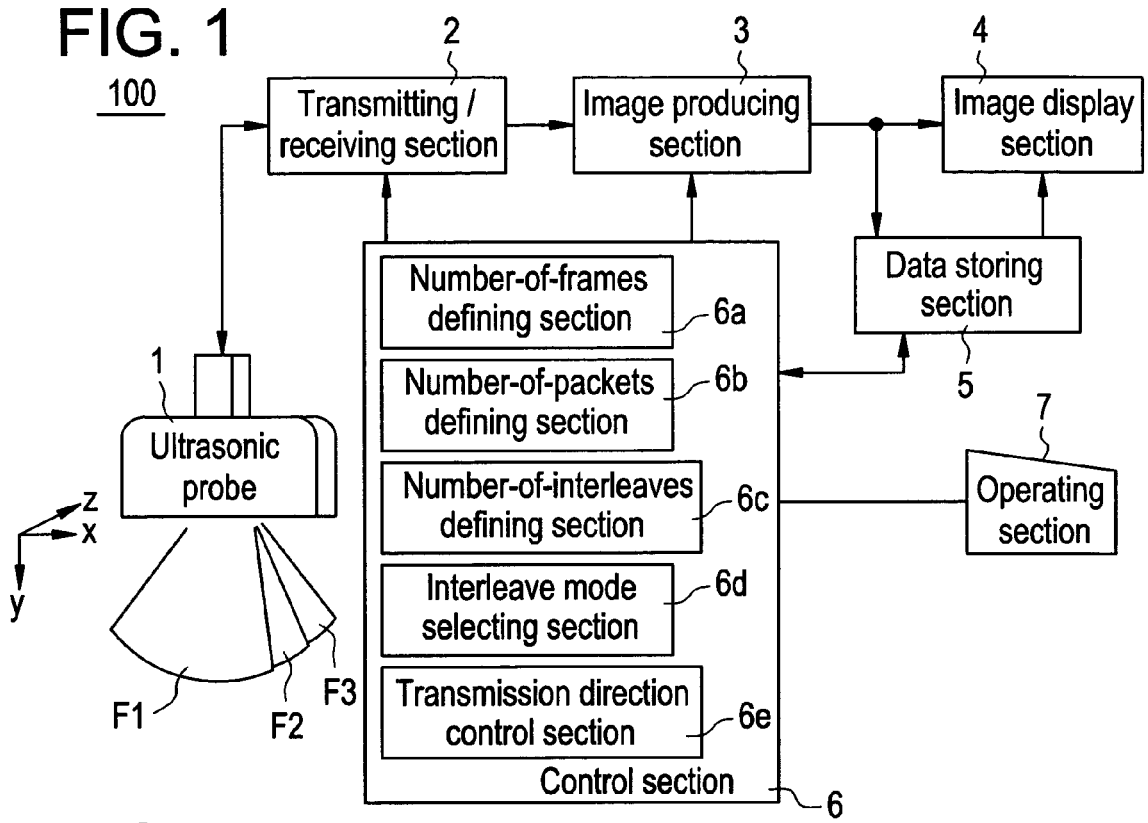
FIG. 1 is a configuration diagram showing an ultrasonic diagnostic apparatus in accordance with one embodiment of the present invention.

FIG. 1 is a configuration diagram of an ultrasonic diagnostic apparatus 100 in accordance with one embodiment of the present invention.

The ultrasonic diagnostic apparatus 100 comprises an ultrasonic probe 1, a transmitting/receiving section 2 for driving the ultrasonic probe 1 to transmit ultrasonic pulses in a desired transmission direction and receive echoes and outputting received data, a signal processing section 3 for producing an ultrasonic image from the received data, an image display section 4 for displaying the image, a data storing section 5 for storing the image and three-dimensional data, a control section 6 for controlling the overall operation, and an operating section 7 for an operator to define the number of packets P and the like, and supply instructions.

The control section 6 comprises a number-of-frames defining section 6a for defining a number of frames based on instructions by the operator, a number-of-packets defining section 6b for defining a number of packets P based on instructions by the operator, a number-of-interleaves defining section 6c for defining a number of interleaves I based on instructions by the operator, an interleave mode selecting section 6d for selecting an interleave mode from between an intra-frame mode and an inter-frame mode based on instructions by the operator, and a transmission direction control section 6e for controlling the ultrasonic pulse transmission direction based on the defined conditions.

The ultrasonic probe 1 is a two-dimensional array ultrasonic probe that electronically changes the ultrasonic pulse transmission direction among acoustic line signals that belong to the same frame, and also electronically changes the ultrasonic pulse transmission direction among acoustic line signals that belong to different frames.

The ultrasonic probe may be one that mechanically changes the ultrasonic pulse transmission direction among acoustic line signals that belong to different frames.

Figure 2:
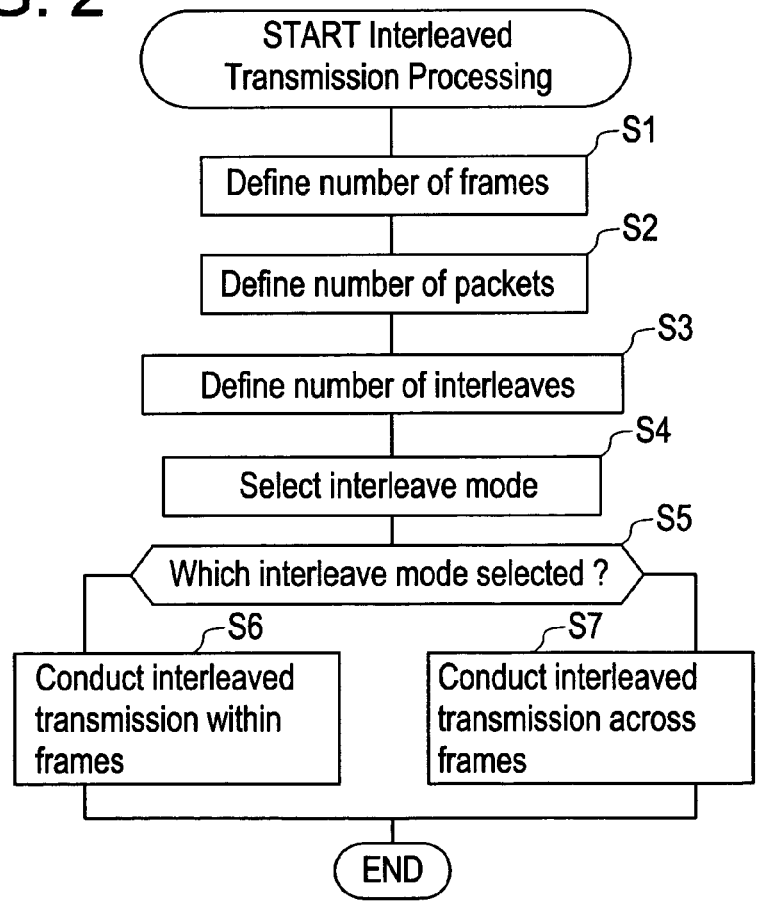
FIG. 2 is a flow chart showing interleaved transmission processing in accordance with one embodiment of the present invention.

FIG. 2 is a flow chart showing interleaved transmission processing by the ultrasonic diagnostic apparatus 100.

At Step S1, the number-of-frames defining section 6a defines a number of frames. Here, it is assumed that a number of frames=3 is defined. In this case, three-dimensional data will be collected by scanning three frames: first frame F1, second frame F2, and third frame F3, as shown in FIG. 1.

Figure 3A:
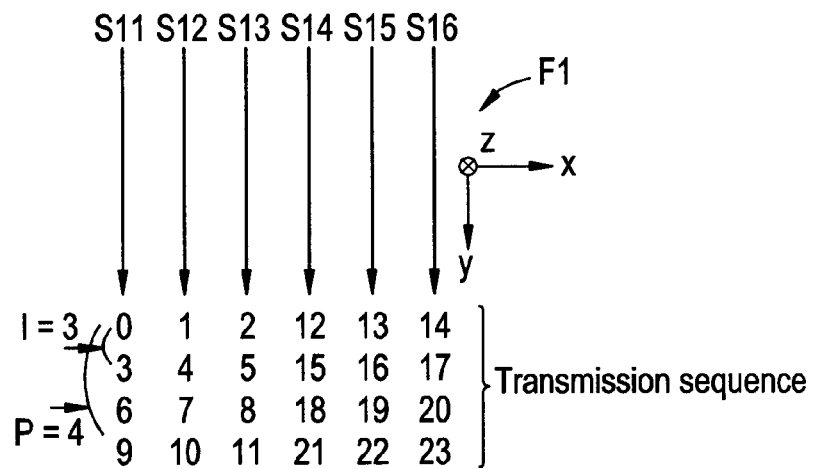
FIG. 3 is an explanatory diagram showing intra-frame mode interleaving.
Figure 3B:
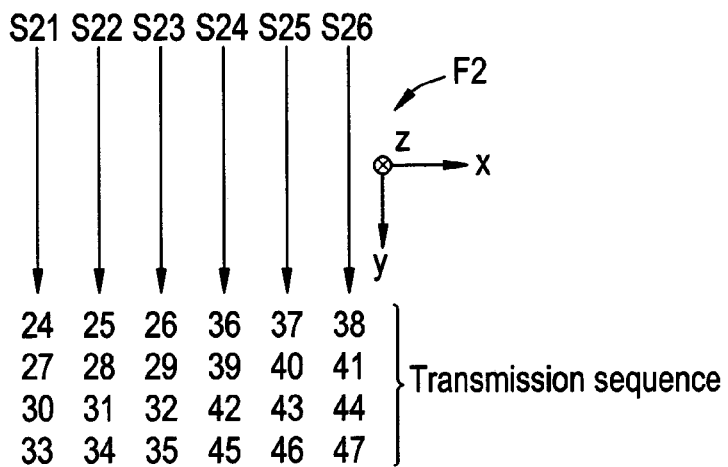
Figure 3C:
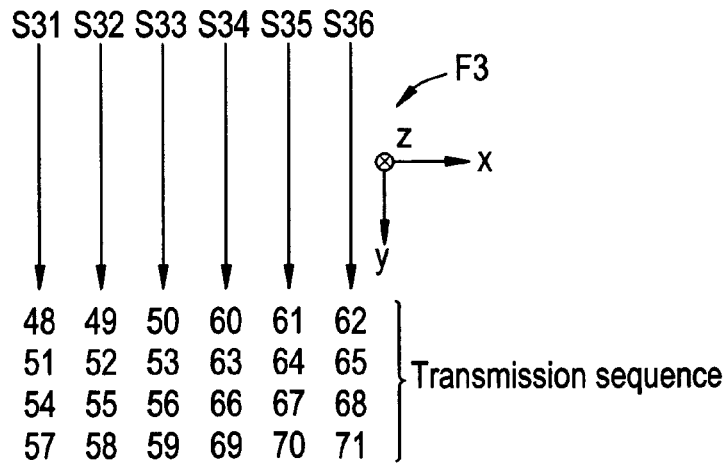
Figure 4A:
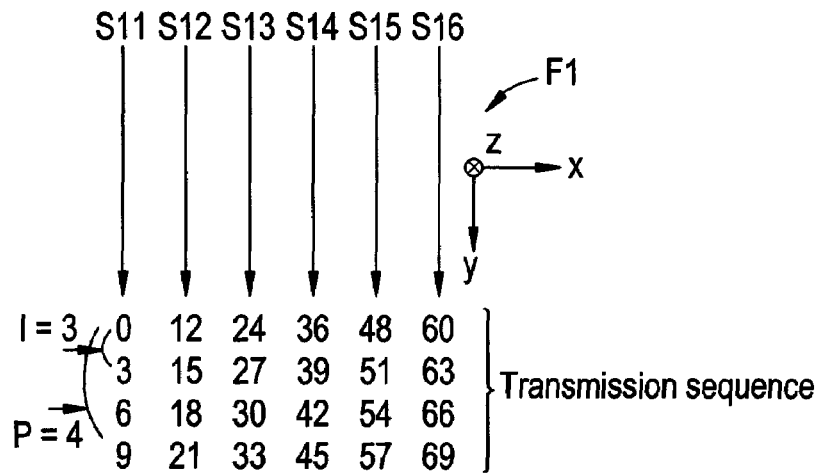
FIG. 4 is an explanatory diagram showing inter-frame mode interleaving.
Figure 4B:
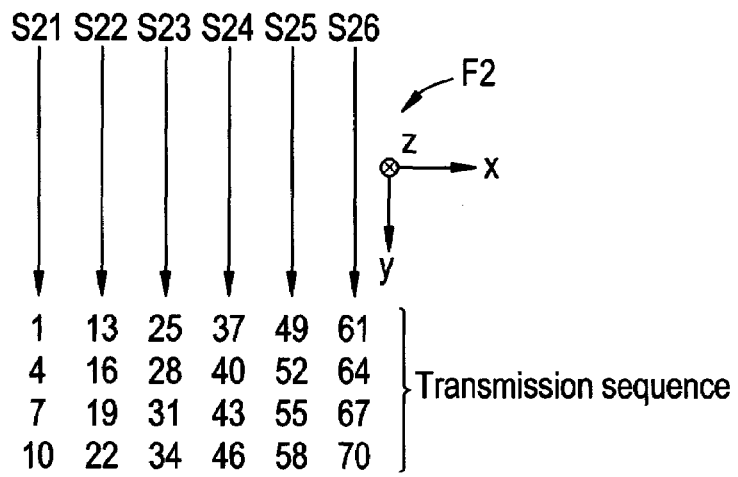
Figure 4C:
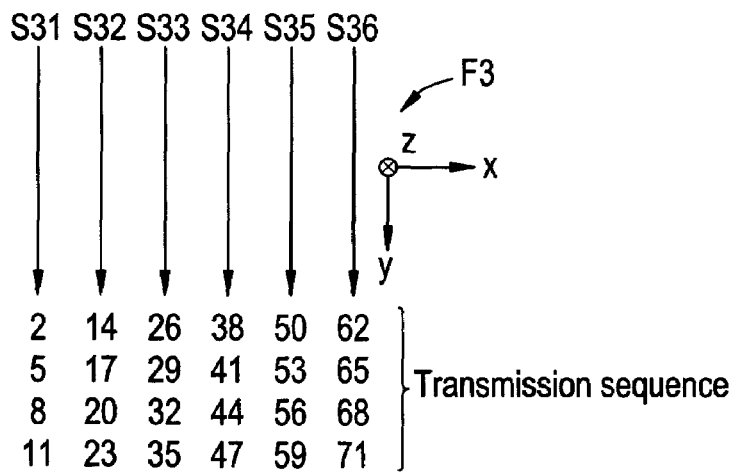

At Step S2, the number-of-packets defining section 6b defines a number of packets P. Here, it is assumed that a number of packets P=4 is defined. In this case, one acoustic line signal will be acquired by conducting four ultrasonic pulse transmissions in one transmission direction, as shown in FIGS. 3 and 4.

At Step S3, the number-of-interleaves defining section 6c defines a number of interleaves I. Here, it is assumed that a number of interleaves I=3 is defined. In this case, each ultrasonic pulse transmission in one transmission direction is interleaved with ultrasonic pulse transmissions in two other transmission directions, as shown in FIGS. 3 and 4.

At Step S4, the interleave mode selecting section 6d prompts the operator to select an interleave mode.

Alternatively, a configuration may be adopted such that when a projection image of three-dimensional data is produced and displayed in real-time, for example, the interleave mode selecting section 6d automatically selects a mode according to the projection direction, e.g., selects an inter-frame mode if the angle between a projection direction and the frame is 45 degrees or more, and selects an intra-frame mode if the angle between the projection direction and a frame is less than 45 degrees.

At Step S5, if the intra-frame mode is selected, the flow proceeds to Step S6, and if the inter-frame mode is selected, the flow proceeds to Step S7.

At Step S6, an intra-frame interleaving scan is conducted. The intra-frame interleaving scan will be described later with reference to FIG. 3.

At Step S7, an inter-frame interleaving scan is conducted. The inter-frame interleaving scan will be described later with reference to FIGS. 4-7.

By conducting the interleaving scan at Step S6 or S7, three-dimensional CF (color flow) or B-flow data are collected in real-time, and a projection image is produced from the three-dimensional data for display.

FIG. 3 is an explanatory diagram of an intra-frame interleaving scan.

Assuming that the number of packets P=4, the number of interleaves I=3, a first frame F1 is composed of sequentially lined-up acoustic lines S11-S16, a second frame F2 is composed of sequentially lined-up acoustic lines S21-S26, and a third frame F3 is composed of sequentially lined-up acoustic lines S31-S36, then ultrasonic pulse transmissions are conducted by cyclically repeating the process below. The numbers in parentheses are indices indicating the order of transmission.

(0) S11-(1) S12-(2) S13-(3) S11-(4) S12-(5) S13-(6) S11-(7) S12-(8) S13-(9) S11-(10) S12-(11) S13-(12) S14-(13) S15-(14) S16-...-(21) S14-(22) S15-(23) S16-(24) S21-(25) S22-(26) S23-(27) S21-(28) S22-(29) S23-...-(45) S24-(46) S25-(47) S26-(48) S31-(49) S32-(50) S33-...-(69) S34-(70) S35-(71) S36.

In the process of FIG. 3, the acoustic lines S11-S13 in the first frame F1, the acoustic lines S14-S16 in the first frame F1, the acoustic lines S21-S23 in the second frame F2, the acoustic lines S24-S26 in the second frame F2, the acoustic lines S31-S33 in the third frame F3, and the acoustic lines S34-S36 in the third frame F3 constitute respective interleave blocks. Thus, when a projection image in a projection direction orthogonal to a frame is observed, for example, the interleave blocks are sometimes noticeable on an image. Accordingly, the interleave mode may be changed to an inter-frame mode in such a case.

FIG. 4 is an explanatory diagram of an inter-frame interleaving scan.

Assuming that the number of packets P=4, the number of interleaves I=3, a first frame F1 is composed of sequentially lined-up acoustic lines S11-S16, a second frame F2 is composed of sequentially lined-up acoustic lines S21-S26, and a third frame F3 is composed of sequentially lined-up acoustic lines S31-S36, then ultrasonic pulse transmissions are conducted by cyclically repeating the process below. The numbers in parentheses are indices indicating the order of transmission.

(0) S11-(1) S21-(2) S31-(3) S11-(4) S21-(5) S31-(6) S11-(7) S21-(8) S31-(9) S11-(10) S21-(11) S31-(12) S12-(13) S22-(14) S32-...-(69) S16-(70) S26-(71) S36.

In the process of FIG. 4, no interleave block is formed in the frames F1, F2 and F3. Thus, when a projection image in a projection direction orthogonal to a frame is observed, for example, the interleave blocks are never noticeable on an image.

FIG. 5 shows a case in which the inter-frame mode is applied to a multi-beam technique for transmitting ultrasonic pulses simultaneously in different transmission directions.

The equally numbered indices in the transmission sequence in FIG. 5 represent simultaneous ultrasonic pulse transmissions.

By using the multiple beams, the frame rate can be improved.

Figure 6A:
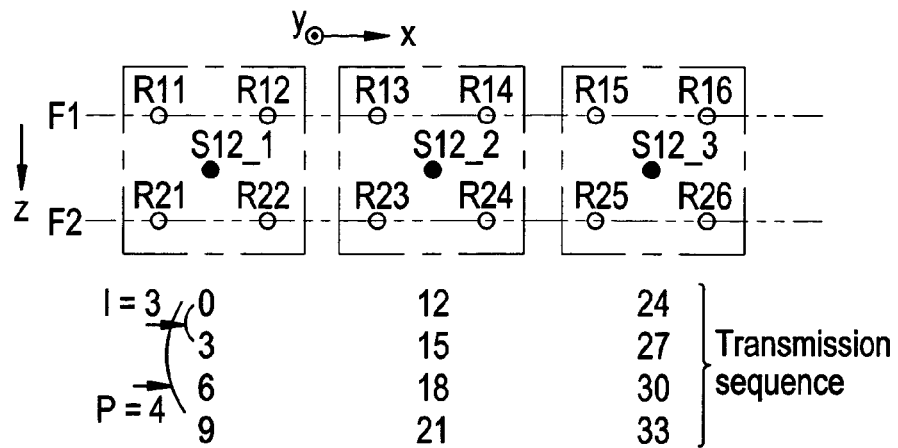
FIG. 6 is an explanatory diagram showing a case in which the inter-frame mode is applied when reception is conducted with four reception directions corresponding to one transmission direction.
Figure 6B:
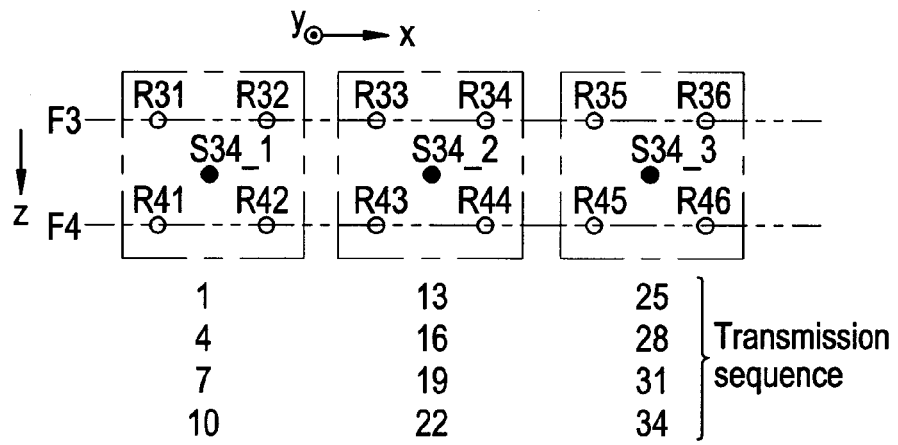
Figure 6C:
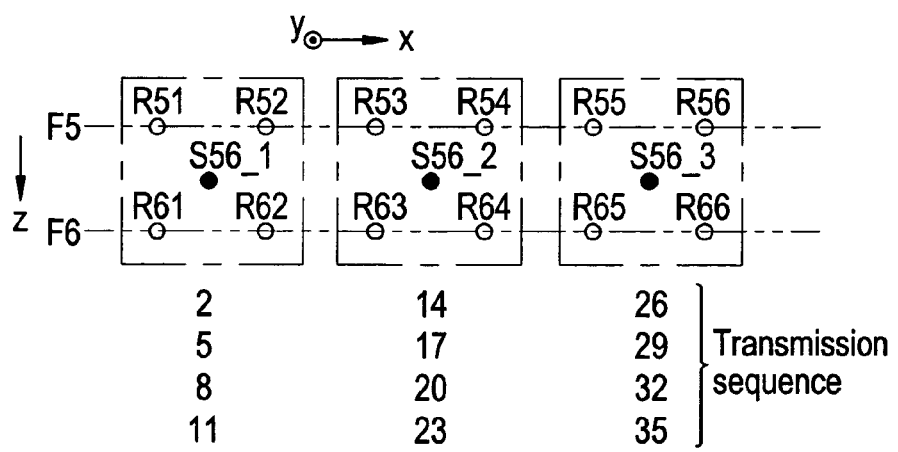

FIG. 6 shows a case in which the inter-frame mode is applied when an ultrasonic pulse is transmitted in one transmission direction and acoustic line signals in four reception directions (each enclosed by a dot-dash line box) corresponding to the transmission direction are simultaneously acquired.

S12_1, S12_2, S12_3, ... represent transmission positions (x-z positions), R11, R12, R13, ... represent reception positions (x-z positions), and F1, F2, ... represent frame positions (x-z positions).

By focusing on transmission directions S12_1, S12_2, S12_3, ..., S56_3, it can be seen that the transmission sequence is equivalent to that of FIG. 4.

Figure 7A:
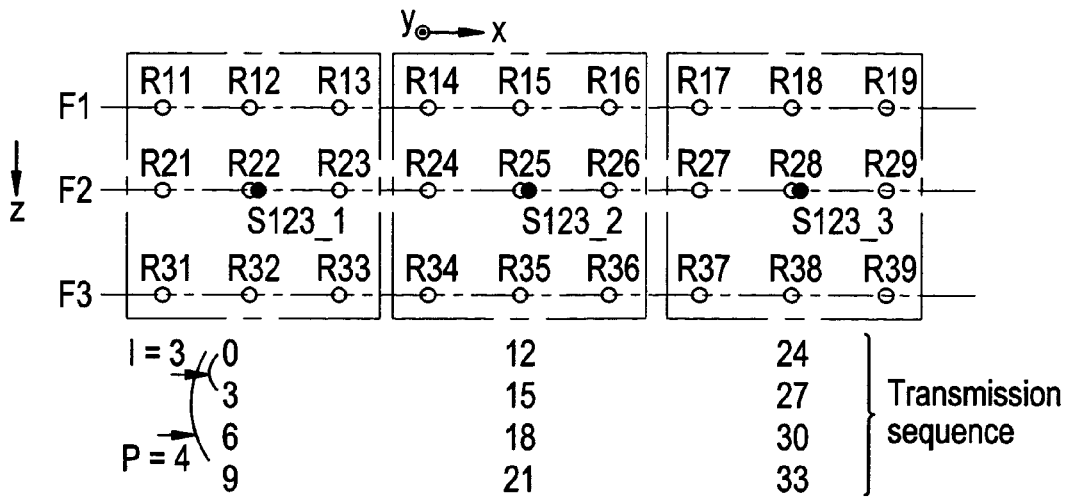
FIG. 7 is an explanatory diagram showing a case in which the inter-frame mode is applied when reception is conducted with nine reception directions corresponding to one transmission direction.
Figure 7B:
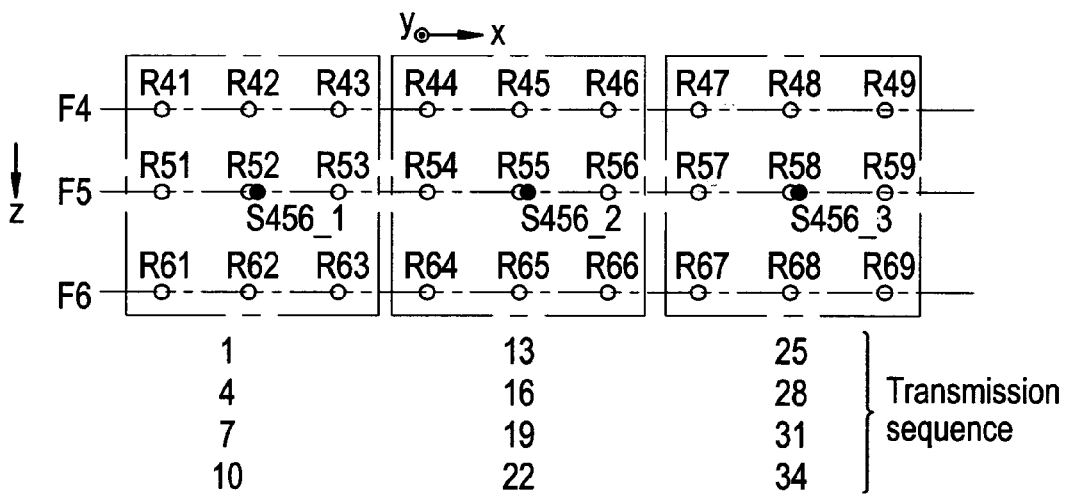
Figure 7C:
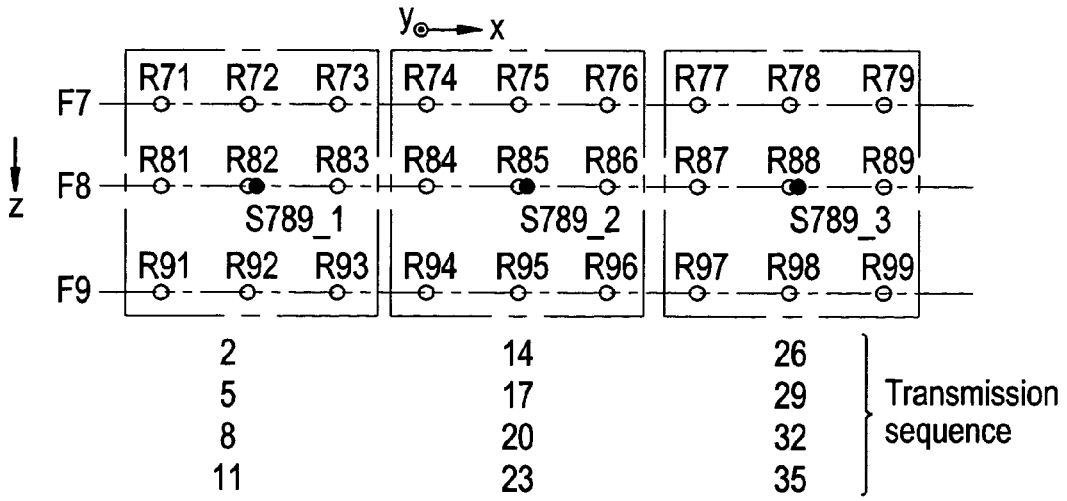

FIG. 7 shows a case in which the inter-frame mode is applied when an ultrasonic pulse is transmitted in one transmission direction and acoustic line signals in nine reception directions (each enclosed by a dot-dash line box) corresponding to the transmission direction are simultaneously acquired.

S123_1, S123_2, S123_3, ... represent transmission positions (x-z positions), R11, R12, R13, ... represent reception positions (x-z positions), and F1, F2, ... represent frame positions (x-z positions).

By focusing on transmission directions S123_1, S123_2, S123_3, ..., S789_3, it can be seen that the transmission sequence is equivalent to that of FIG. 4.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic diagnostic apparatus comprising:
an ultrasonic probe;
a number-of-frames defining device for defining a number of frames f;
a transmitting/receiving device for driving said ultrasonic probe to conduct P ultrasonic pulse transmissions in one direction and receive echoes to acquire a first acoustic line signal, wherein P is at least equal to two;
a transmission direction control device for controlling the transmission direction in an intra-frame mode in which the transmission direction is controlled to interleave at least one ultrasonic pulse transmission for acquiring a second acoustic line signal that belongs to the frame to which said first acoustic line signal belongs between the ultrasonic pulse transmissions in said one direction, or in an inter-frame mode in which the transmission direction is controlled to interleave at least one ultrasonic pulse transmission for acquiring a third acoustic line signal that belongs to a frame different from that to which said first acoustic line signal belongs between the ultrasonic pulse transmissions in said one direction; and
an interleave mode selecting device for an operator to select between said intra-frame mode and inter-frame mode.

2. The ultrasonic diagnostic apparatus of claim 1, wherein said apparatus comprises a number-of-interleaves defining device for defining a number of interleaves I ($\geq 2$), and said transmission direction control device controls the transmission direction to interleave ultrasonic pulse transmissions for acquiring (I−1) other acoustic line signals that belong to the frame to which said first acoustic line signal belongs between the ultrasonic pulse transmissions in said one direction, or to interleave ultrasonic pulse transmissions for acquiring (I−1) acoustic line signals that belong to (I−1) frames different from the frame to which said first acoustic line signal belongs between the ultrasonic pulse transmissions in said one direction.

3. The ultrasonic diagnostic apparatus of claim 1, wherein said ultrasonic probe is a two-dimensional array ultrasonic probe, and said transmission direction control device electronically changes the ultrasonic pulse transmission direction among acoustic line signals that belong to the same frame, and also electronically changes the ultrasonic pulse transmission direction among acoustic line signals that belong to different frames.

4. The ultrasonic diagnostic apparatus of claim 1, wherein said apparatus comprises a mechanism that can mechanically change orientation of said ultrasonic probe in a direction orthogonal to a frame, and said transmission direction control device electronically changes the ultrasonic pulse transmission direction among acoustic line signals that belong to the same frame, and mechanically changes the ultrasonic pulse transmission direction among acoustic line signals that belong to different frames.

5. The ultrasonic diagnostic apparatus of claim 1, wherein said transmitting/receiving device conducts ultrasonic pulse transmissions simultaneously in different directions to simultaneously acquire a plurality of acoustic line signals.

6. The ultrasonic diagnostic apparatus of claim 1, wherein said transmitting/receiving device acquires acoustic line signals containing flow information.

* * * * *